US006730707B2

(12) United States Patent
Pintor et al.

(10) Patent No.: US 6,730,707 B2
(45) Date of Patent: May 4, 2004

(54) METHOD FOR REDUCING INTRAOCULAR PRESSURE USING INDOLE DERIVATIVES

(75) Inventors: Jesus J. Pintor, Madrid (ES); Maria A. Peral, Madrid (ES); Ward M. Peterson, Durham, NC (US); Robert Plourde, Jr., Chapel Hill, NC (US); Edward G. Brown, Apex, NC (US); Benjamin R. Yerxa, Raleigh, NC (US)

(73) Assignees: Inspire Pharmaceuticals, Inc., Durham, NC (US); Universidad Complutense de Madrid, Madrid (ES)

( * ) Notice: Subject to any disclaimer, the term of this patent is extended or adjusted under 35 U.S.C. 154(b) by 7 days.

(21) Appl. No.: 09/915,486

(22) Filed: Jul. 25, 2001

(65) Prior Publication Data

US 2002/0037887 A1 Mar. 28, 2002

Related U.S. Application Data

(60) Provisional application No. 60/276,885, filed on Mar. 16, 2001.

(30) Foreign Application Priority Data

Jul. 28, 2000 (ES) .............................. 20001916

(51) Int. Cl.[7] ......................... A61K 47/32; A61K 31/55
(52) U.S. Cl. ..................... 514/772.4; 514/215; 514/220
(58) Field of Search .............................. 514/772.4, 215, 514/220

(56) References Cited

U.S. PATENT DOCUMENTS

| 4,654,361 A | 3/1987 | Samples et al. |
| 4,803,218 A | 2/1989 | Stanley et al. |
| 5,219,849 A | 6/1993 | Lotti et al. |
| 5,545,626 A | 8/1996 | Stein et al. |
| 5,633,276 A | 5/1997 | North et al. |
| 5,948,804 A | 9/1999 | Jeon et al. |
| 6,004,991 A | 12/1999 | Fourtillan et al. |
| 6,040,451 A | 3/2000 | Jeon et al. |
| 6,071,946 A | 6/2000 | Lesieur et al. |
| 6,140,372 A | 10/2000 | Fourtillan et al. |
| 6,159,998 A | 12/2000 | Jeon et al. |
| 6,268,359 B1 * | 7/2001 | Ogawa et al. ............... 514/215 |

FOREIGN PATENT DOCUMENTS

| WO | WO 89/01472 | * 2/1989 |
| WO | WO 96/11685 | 4/1996 |
| WO | WO 96/25397 | 8/1996 |
| WO | WO 00/03741 | 1/2000 |

OTHER PUBLICATIONS

Pintor, et al., "Involvement of melatonin Mt3 receptors in the regulation of intraocular pressure in rabbits," *Euro. J. Phamracology.* 416:251–254 (2001).
Samples, et al., "Effect of melatonin on intraocular pressure," *Current Eye Research* 7(7):649–653 (1988).
Aimoto et al., *J. Ocul Pharmacol.* 1:149–160 (1985).
Axelsson et al., "The Frequency of Cataract After Miotic Therapy", *Acta. Ophthalmol.* (Kbh). 44:421–429 (1966).
Boger III et al., "Clinical Trial Comparing Timolol Ophthalmic Solution to Pilocarpine in Open–Angel Glaucoma", *Am. J. Ophthalmol.* 86:8–18 (1978).
Chiou et al., "Studies on the Involvement of Melatonergic Mechanism in Intraocular Pressure Regulation", *Ophthalmic Res.*, 16:302–306 (1984).
Chiou et al., "Melatonergic Involvement in Diurnal Changes of Intraocular Pressure in Rabbit Eyes", *Ophthalmic Res.*, 17:373–378 (1985).
de Roetth, "Lenticular Opacities in Glaucoma Patients Receiving Echoothiophate Iodid Therapy", *JAMA*, 195:664–666 (1966).
Dkhissi et al, "Day and Night Dysfunction in Intraretinal Melatonin and Related Indoleamines Metabolism, Correlated with the Development of Glaucoma–Like Disorder in an Avian Model", *J. Neuroendocrinol*, 10:863–869 (1998).
Dubocovich et al., "Selective $MT_2$ melatonin receptor antagonists block melatonin–mediated phase advances of circadian rhythms", *FASEB J.*, 12:1211–1220 (1998).
Higginbotham, "Will Latanoprost Be the 'Wonder' Drug of the '90s for the Treatement of Glaucoma," *Arch. Ophthalmol.* 114:998–999 (1996).

Kaufman et al., "Chollinergics", *Handbook of Experiemental Pharmacology*, 69:149–192 (1984).
Kiuchi et al., "Melatonin does not increase IOP significantly in rabbits", *Curr. Eye Res.* 12:181–190 (1993).
Laties, "Localization in Cornea and Lens of Topically–Applied Irreversible Cholinesterase Inhibitors", *Aj. J. Ophthalmol.* 68:848–847 (1969).
Lotti et al., "Autonomic Nervous Systems: Adrenergic Antagonists, *Handbook of Experimental Pharmacology*", 69:249–278 (1984).
Marco et al., "Melatonin", *Current Medicinal Chemistry*, 6:501–518 (1999).
Meyer–Bothling et al, "Topical Application of Serotonin or the 4–HT$_1$–Agonist 5–CT Intraocular Pressure in Rabbits", *Invest Ophthalmol. Vis. Sci.* 34:3035–3042 (1993).
Molinari et al., "2–[$^{125}$I] Iodo–5–methoxycarbonylamino–N–acetyltryptamine: a selective radioligand for the characterization of melatonin ML$_2$ binding sites", *European J. Pharmacol.* 301:159–168 (1996).
Mullins et al., "Melatonin Agonists Induce Phosphoinositide Hydrolysis in Xenopus Laevis Melanophores", *Cell Signal*, vol. 9, No. 2, pps. 169–173 (1997).
Osborne, "Serotonin and melatonin in the iris/ciliary processes and their involvement in intraocular pressure", *Acta Neurobiol. Exp.* (Warsa) 54 Suppl: pps. 57–64 (1994).
PDR for Ophthalmic Medicines, pps. 314–316 (2001).
Ritch, "Neuroprotection: is it already applicable to glaucoma therapy?" *Curr. Opin. Ophthalmol.* 11:78–84 (2000).
Rhode et al., "Effects of Melatonin and Haloperiodol Given via Vortex Vein on the Intraocular Pressure", *Ophthalmic Res.* 25:10–15 (1993).
Rohde et al., *"Existence and Role of Endogenous ocular Melatonin"*, *J. Ocul. Pharmacol.* 1:235–243 (1985).
Schwartz, "Current Concepts in Ophthallmology", *N. England J. Med.*, 290:182–184 (1978).
Serle, "Pharmacological Advances in the Treatment of Glaucoma", Drugs Aging 5:156–170 (19949).
Shaffer et al., "Anticholinesterase Drugs and Cataracts", Am. J. Ophthalmol. 62:613–618 (1966).
Wilsoet et al., "Investigation of parameters influencing intraocular pressure increases during sleep", *Ophthalmic. Physiol. Opt.* 13:356–365 (1993).

* cited by examiner

*Primary Examiner*—Thurman K. Page
*Assistant Examiner*—Blessing Fubara
(74) *Attorney, Agent, or Firm*—Albert P. Halluin; Viola T. Kung; Howrey, Simon, Arnold & White, LLP

(57) ABSTRACT

The present invention provides a method of reducing intraocular pressure by administering pharmaceutical compositions comprising indole derivatives. The pharmaceutical compositions useful in this invention comprise indole derivatives and melatonin analogs of Formulae I–IV. A preferred embodiment is a method of lowering intraocular pressure using 5-(methoxycarbonylamino)-N-acetyltryptamine (5-MCA-NAT), also known as GR 135531, which has a prolonged duration of action and greater efficacy in lowering intraocular pressure compared to melatonin. The present invention further provides a method of treating disorders associated with ocular hypertension, and a method of treating various forms of glaucoma; the method comprises administering an effective dose of a pharmacuetical composition comprising an indole derivative with or without agents commonly used to treat such disorders.

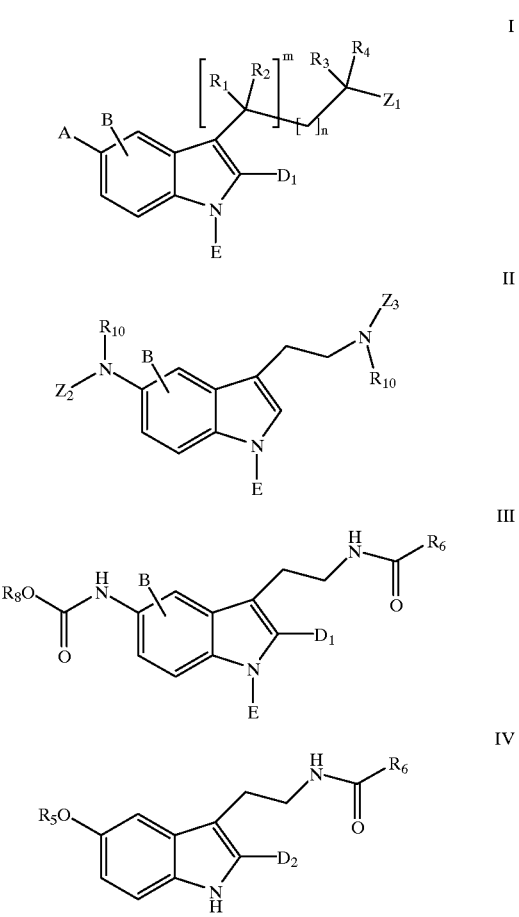

24 Claims, 4 Drawing Sheets

METHOD FOR REDUCING INTRAOCULAR PRESSURE USING INDOLE DERIVATIVES

This application claims the benefit of Spanish Application No. P200001916, filed Jul. 28, 2000. This application also claims the benefit of U.S. Provisional Application Ser. No. 60/276,885, filed Mar. 16, 2001.

TECHNICAL FIELD

This invention relates to a method for lowering intraocular pressure, treating ocular hypertension, and treating glaucoma, by administering indole analogues and pharmaceutical compositions.

BACKGROUND OF THE INVENTION

Glaucoma is a slowly progressive blinding disease usually associated with chronic elevation of intraocular pressure (IOP). Sufficiently high and persistent intraocular pressure is believed to result in damage to the optic disc at the juncture of the optic nerve and retina, resulting in degeneration of retinal ganglion cells and blindness characteristic of glaucoma. However, the mechanism whereby IOP elevation (also known as ocular hypertension) leads to glaucoma is not well understood. Additionally, a fraction of patients with typical visual field loss associated with glaucoma do not show abnormal elevated IOP levels (known as low-tension or normal-tension glaucoma).

Glaucoma is primarily classified as open-angle, closed-angle, or congenital, and further classified as primary and secondary. Glaucoma is treated with a variety of pharmacological and surgical approaches. In cases where glaucoma is associated with ocular hypertension, pharmacological treatment comprises adrenergic agonists (epinephrine, dipevefrin, apraclonidine), cholinergic agonists (pilocarpine), beta blockers (betaxolol, levobunolol, timolol), carbonic anhydrase inhibitors (acetazolamide) or more recently, prostaglandin analogues (latanoprost, bimatoprost (Lumigan™)) and alpha adrenergic agonists (brimonidine). These pharmacological approaches help restore the IOP to a normotensive state either by inhibiting the production of aqueous humor by the ciliary body, or facilitating trabecular or uveoscleral aqueous humor outflow. Anticholinergic agents reduce intraocular pressure in primary glaucoma, reducing the resistance to outflow of the aqueous humor outflow. Anticholinesterase inhibitors have been used to manage primary and certain forms of secondary glaucoma, such as aphakic glaucoma following cataract extraction. The congenital form of glaucoma rarely responds to therapy and is more commonly treated with surgery. In narrow angle glaucoma, the aqueous outflow is enhanced by freeing of the entrance to the trabecular space at the canal of Schlemm from blockade by the iris, as a result of the drug-induced contraction of the sphincter muscle of the iris. (Taylor, pp. 123–125, in The *Pharmacological Basis of Therapeutics*, 7$^{th}$ Ed, Eds., A. G. Gilman, L. S. Goodman, T. W. Rail, and F. Murad, MacMillan Publishing Company, New York, (1985)).

In wide-angle, or chronic simple glaucoma, the entry to the trabeculae is not physically obstructed; the trabeculae, a meshwork of pores of small diameter, lose their patency. Contraction of the sphincter muscle of the iris and the ciliary muscle enhances tone and alignment of the trabecular network to improve resorption and outflow of aqueous humor through the network to the canal of Schlemm (Watson, *Br. J. Opthalmol.* 56: 145–318 (1972); Schwartz, *N. Engl. J. Med.*, 290: 182–186 (1978); Kaufman, et al., *Handbook of Experimental Pharmacology* 69: 149–192 (1984)).

Acute congestive (narrow angle) glaucoma is nearly always a medical emergency in which the drugs are essential in controlling the acute attacks, but long-range management is usually based predominantly on surgery (peripheral or complete iridectomy). By contrast, chronic simple (wide-angle) glaucoma has a gradual, insidious onset and is not generally amenable to surgical improvement; and control of intraocular pressure depends upon permanent therapy.

Acute congestive glaucoma may be precipitated by the injudicious use of a mydriatic agent in patients over 40 years, or by a variety of factors that can cause pupillary dilatation or engorgement of intraocular vessels. Signs and symptoms include marked ocular inflammation, a semidilated pupil, severe pain, and nausea. The therapeutic objective is to reduce the intraocular pressure to the normal level for the duration of the attack. An anticholinesterase agent is instilled into the conjunctival sac in combination with a parasympathomimetic agent for greatest effectiveness. A commonly used combination consists of a solution of physostigmine and salicylate, 0.5%, plus pilocarpine nitrate, 4%. Adjunctive therapy includes the intravenous administration of a carbonic anhydrase inhibitor such as acetozolamide to reduce the secretion of aqueous humor, or of an osmotic agent such as mannitol or glycerin to induce intraocular dehydration. The long-acting organophosphorus compounds are not indicated in narrow-angle glaucoma because of vascular engorgement and increase in the angle block.

Therapy of chronic simple glaucoma and secondary glaucoma includes: (1) parasympathomimetic agents (e.g. pilocarpine nitrate, 0.5 to 0.6%); (2) anticholinesterase agents that are short-acting (e.g. physostigmine salicylate, 0.25 and 0.5%) or long-acting (demecarium bromide, 0.125 to 0.25%; echothiophate iodide, 0.03 to 0.25%; isoflurophate, 0.025%); (3) beta-adrenergic antagonists such as timolol maleate, a long-acting agent that is administered at 12-hour intervals, does not directly affect pupillary aperture, but reduces production of aqueous humor (Boger, et al., *Am. J Opthalmol.* 86: 8–18 (1978); Lotti, et al., *Handbook of Experimental Pharmacology* 69: 249–278 (1984)) and avoids the partial block of accommodation and the untoward effects of the long-acting anticholinesterase agents; and, paradoxically, (4) sympathomimetic agents (e.g. epinephrine, 0.25 to 2%, phenylephrine, 10%), which are most effective when used in combination with anticholinesterase inhibitors or cholinergic agonists. They reduce intraocular pressure by decreasing secretion of the aqueous humor, and prevent engorgement of the small blood vessels.

Because the cholinergic agonists and cholinesterase inhibitors block accommodation, they induce transient blurring of far vision, usually after administration of relatively high doses over shorter duration. With long-term administration of the cholinergic agonists and anticholinesterase agents, the response diminishes due to a diminished number of acetylcholine receptors.

Despite the convenience of less frequent administration and the high potency of long-acting anticholinesterase agents, the use of long-acting anticholinesterase agents is associated with a greater risk of developing lenticular opacities and untoward autonomic effects. An organophosphorus agent, DFP, has the longest duration of action and is extremely potent when applied locally; solutions in peanut or sesame oil require installation from once daily to once weekly, and may control intraocular pressure in severe cases that are resistant to other drugs. Because the oily vehicle is unpleasant to most patients, DFP has been replaced by echothiophate.

Treatment of glaucoma with potent, long-acting anticholinesterase agents (including demecarium, echothiophate, and isoflurophate) for 6 months or longer is associated with a high risk of developing cataracts. (Axelsson, et al., *Acta Opthalmol. (Kbh.)* 44: 421–429 (1966); de Roetth, *J.A.M.A.* 195: 664–666 (1966); Shaffer, et al., *Am. J. Opthalmol.* 62: 613–618 (1966)) Although development of cataracts is common in untreated comparable age groups, the incidence of lenticular opacities under such circumstances can reach 50%, with the risk increasing in proportion to the strength of the solution, frequency of installation, duration of therapy, and age of patient. (Laties, *Am. J Opthalmol.* 68: 848–857 (1969); Kaufman, et al., pp. 149–192, in *Pharmacology of the Eye, Handbook of Experimental Pharmacology*, Vol. 69, Ed. M. L. Sears, Springer-Verlag, Berlin, (1984)).

Long-acting anticholinesterase agents are not recommended when glaucoma can be controlled by timolol, parasympathomimetic drugs, physostigmine, or other agents. Nevertheless, the long-acting cholinesterase inhibitors retain their therapeutic importance in situations where other agents are inadequate, since glaucoma may lead to irreversible blindness if not adequately controlled.

Treatment with pilocarpine (4%) alone or in combination with physostigmine (0.2%) one to five times daily was found to cause no higher incidence of the development of lenticular opacities that appeared spontaneously in untreated patients in comparable age groups (Axelsson, *Acta Opthalmol.* (Kbh., Suppl. 102, 1–37 (1969)). Thus, pilocarpine and other short-acting miotic drugs can be used to control intraocular tension. If ineffective, the hazards of cataract development must be balanced against those of increased intraocular pressure before resorting to the use the potent, long-acting anticholinesterase agents. However, patients should be examined for the appearance of lenticular opacities at intervals of 6 months or less.

Other new agents have been assessed for treatment of glaucoma, including an $A_3$ subtype adenosine receptor antagonist, a calmodulin antagonist, and an antiestrogen (WO 00/03741); an oligonucleotide which may be substituted, or modified in its phosphate, sugar, or base so as to decrease intraocular pressure (U.S. Pat. No. 5,545,626); a class of pyrazine, pyrimidine, and pyridazine derivatives, substituted by a non-aromatic azabicyclic ring system and optionally by up to two further substituents (U.S. Pat. No. 5,219,849); and Latanoprost, a prostacyclin analogue (Higginbotham, *Arch. Opthalmol.* 114: 998–999 (1996)). Four classes of compounds with promising clinical potential for the long-term management of glaucoma include topically active carbonic anhydrase inhibitors, selective alpha-2 adrenergic agonists, prostaglandins, and ethacrynic acid (Serle, *Drugs Aging* 5: 156–170 (1994)).

Miscellaneous ocular side effects that may occur following instillation of anticholinesterase agents are headache, brow pain, blurred vision, phacodinesis, pericorneal injection, congestive iritis, various allergic reactions and, rarely, retinal detachment. When anticholinesterase drugs are instilled intraconjunctivally at frequent intervals, sufficient absorption may occur to produce various systemic effects that result from inhibition of anticholinesterase and butyryl-cholinesterase. Hence, cholinergic autonomic function may be enhanced, the duration of action of local anesthetics with an ester linkage prolonged, and succinylcholine-induced neuromuscular blockade enhanced and prolonged. Individuals with vagotonia and allergies are at particular risk.

Latanaprost (Xalatan®) is a prostanoid agonist that is believed to reduce IOP by increasing the uveoscleral outflow of aqueous humor. Latanoprost is an isopropyl ester prodrug, and is hydrolyzed by esterases in the cornea to the biologically active acid. Xalatan® is prescribed for once-daily dosing and is shown to be equivalently effective as twice-daily dosing of 0.5% timolol. Xalatan® may gradually change eye color by increasing the amount of brown pigment in the iris. This long-term effect on the iris is unknown. Eyelid skin darkening has also been reported in associated with the use of Xalatan®. In addition, Xalatan® may gradually increase the length, thickness, pigmentation, and number of eyelashes. Macular edema, including cystoid macular edema, has been reported during treatment with Xalatan®. These reports have mainly occurred in aphakic patients, in pseudophakic patients with a torn posterior lens capsule, or in patients with known risk factors for macular edema. ((Ophthalmic PDR, 315–316 (2001).)

In summary, although a wide variety of pharmaceutical treatments for lowering IOP are available for the glaucoma patient, these treatments are limiting either in terms of efficacy or side-effects.

Melatonin is a neurohormone secreted primarily by the pineal gland and also in small amounts, by the retina. Melatonin production follows a circadian rhythm with levels increasing during the night. Melatonin is known to regulate many aspects of circadian rhythm, such as the processing of periodic information. Its mechanisms of action include the activation of melatonin membrane receptors, classified into three types, $MT_1$ (previously known as $mel_{1a}$), $MT_2$ (previously known as $mel_{1b}$ or $ML_1$) and $MT_3$ (previously known as $ML_2$), and anti-oxidative protection against oxidative injury through radical scavenger activity. Similar to muscarinic and purinergic receptors, $MT_1$ and $MT_2$ receptors belong to the superfamily of putative seven transmembrane domain G-protein coupled receptors. Both $MT_1$ and $MT_2$ receptors have been cloned and are negatively coupled to adenylate cyclase via a pertussis toxin-sensitive G-protein. $MT_3$ has not been cloned and seems to be coupled to phospholipase C. (Mullins, et al., *Cell Signal* 9, 169–173 (1997)) Studies have shown that $MT_1$ receptors mediate rat caudal artery vasoconstriction and inhibition of neuronal firing associated with somnogenic effects, whereas $MT_2$ receptors mediate rat caudal artery vasodilatation and phase advancement of circadian rhythms. (Marco, et al., *Current Medicinal Chemistry* 6, 501–518 (1999)). The $MT_3$ receptor has been characterized using the high affinity ligand, 5-(methoxycarbonyl-amino)-N-acetyltryptamine (5-MCA-NAT), also known as GR 135531 (Molinari, et al., *European J. Pharmacol.* 301, 159–168 (1996)) although no physiological activity was reported.

The involvement of melatonin in regulating intraocular pressure (IOP) is unclear, and previous work has shown that melatonin can increase or decrease IOP, depending on the species and time during circadian rhythm that the IOP is measured. (Chiou and McLaughlin, *Ophthalmic Res.* 16: 302–306 (1984); Rohde, et al., *J. Ocul. Pharmacol.* 1: 235–243 (1985); Chiou, et al., *Ophthalmic Res.* 17: 373–8 (1985); Rohde, et al., *Ophthalmic Res.* 25: 10–15 (1993); Meyer-Bothling, et al., *Invest. Ophthalmol. Vis. Sci.* 34: 3035–3042 (1993); Osborne, *Acta Neurobiol. Exp.* (*Warsz*) 54 Suppl: 57–64 (1994); Aimoto, et al., *J. Ocul. Pharmacol.* 1: 149–160 (1985); Wilsoet, et al., *Ophthalmic Physiol. Opt.* 13: 357–165 (1993); Dkhissi, et al., *J Neuroendocrinol.* 10: 863–869 (1998); Ritch, *Curr. Opin. Opthalmol.* 11: 78–84 (2000); Kiuchi, et al., *Curr. Eye Res.* 12: 181–190 (1993); Dubocovich, et. al., *FASEB J.* 12, 1211–1220 (1998)). The majority of studies show that melatonin increases IOP. However, U.S. Pat. No. 4,654,361 discloses a method of lowering intraocular pressure by administering an effective amount of melatonin. This and other U.S. patents cited herein are hereby incorporated in their entirety.

U.S. Pat. No. 4,803,218 discloses a method of treating hypertension in an animal by administering a pharmaceutical composition comprising a [3-(aminoalkyl)-1H-indol-5-yl]urea compound and a pharmaceutically-acceptable carrier. This patent also teaches methods of making N-[3-(2-Aminoethyl)-1H-indol-5-yl]urea and related analogues. U.S. Pat. Nos. 5,633,276, 6,040,451, 5,948,804 and 6,159,998 disclose methods of using substituted 5-(2-imidazolin-2-ylamino)indole compounds for lowering intraocular pressure, presbyopia, treating migraine, hypertension, alcohol withdrawal, drug addiction, rheumatoid arthritis, ischemic pain, spasticity, diarrhea, nasal decongestion, and urinary incontinence. U.S. Pat. Nos. 6,004,991, 6,140,372, 59,998,461, and 6,071,946 disclose methods of treating complaints associated with melatonin disorders. Methods of syntheses of substituted indole derivatives disclosed in the above-mentioned patents are incorporated herein by reference.

PCT International Application WO 96/25397 discloses indole derivatives active at cannabinoid receptors and their use for lowering intraocular pressure and treating glaucoma. PCT International Application WO 96/11685 discloses indole derivatives for the treatment of glaucoma and other disorders. The indole derivatives disclosed in the above two PCT applications are different from those of the present invention.

As described above, agents commonly used to treat glaucoma may cause adverse side effects, such as the development of cataracts. There exists a need for agents that are both safe and effective in treating glaucoma.

SUMMARY OF THE INVENTION

Disclosed herein is a novel method of reducing intraocular pressure by administering compounds of Formulae I, II, III, and IV, which possess a core indole or melatonin-type chemical structure.

The present invention provides a method of using such compounds for reducing intraocular pressure with increased duration and/or magnitude of action compared to melatonin. A preferred compound is 5-(methoxycarbonylamino)-N-acetyltryptamine (MCA-NAT), also known as GR 135531, (Molinari, et al., Eur. J. Pharmacol. 301, 159–168 (1996)), a high affinity ligand with specificity for the $MT_3$ receptor.

The present invention provides a method of reducing intraocular pressure and treating disorders associated with intraocular pressure such as ocular hypertension and glaucoma. The method comprises the step of administering to a subject in need thereof an indole derivative in an amount effective to reduce intraocular pressure. The indole derivatives of Formulae I, II, III, and IV, have a prolonged duration of action and/or increased efficacy in reducing intraocular pressure.

DETAILED DESCRIPTION OF THE INVENTION

Figure 1:
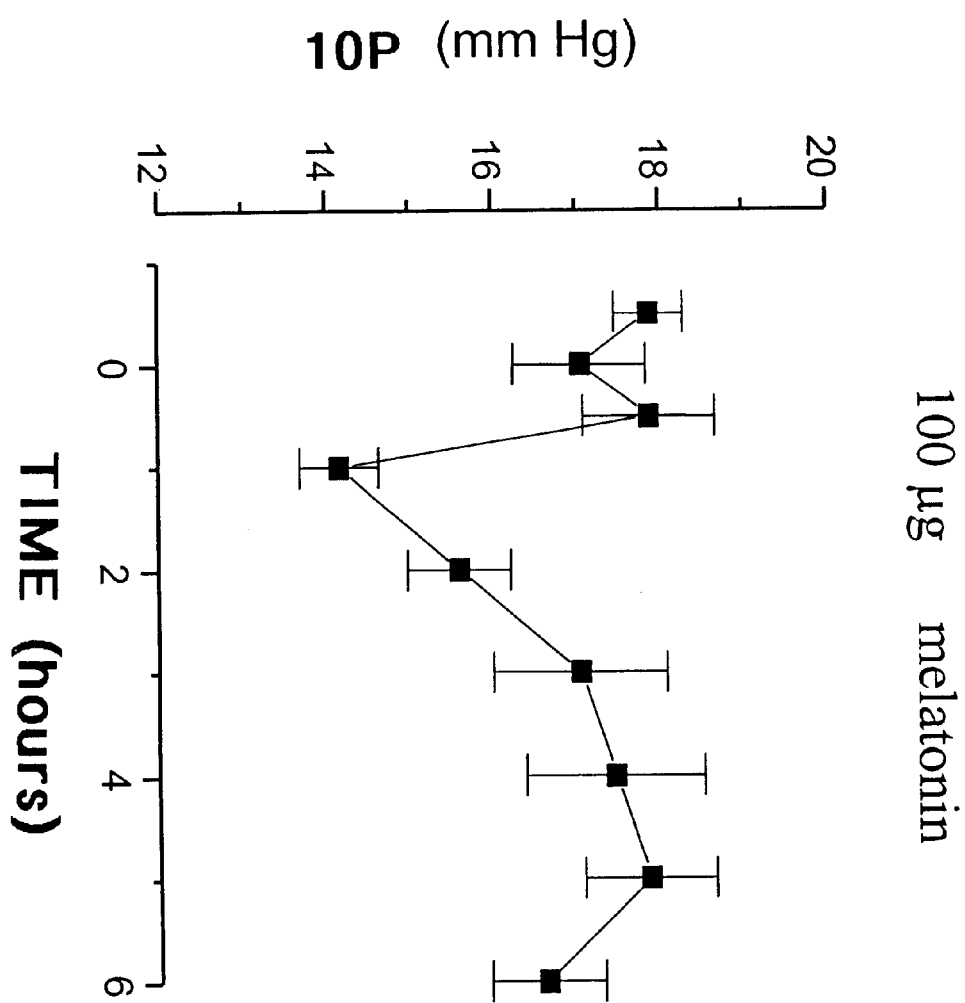
FIG. 1 shows the effect of melatonin on IOP in New Zealand white rabbits during a six hour timecourse.

The present invention provides a method of treating disorders associated with increased intraocular pressure. The method comprises administering an effective dose of an indole derivative of Formulae I, II, III, and IV, with or without therapeutic and adjuvant agents commonly used to treat or manage increased intraocular pressure. Applicants have unexpectedly found that application of such compounds brings about a significant and sustained reduction of intraocular pressure. An effective dose will be the amount of such compound necessary to elicit the reduction of intraocular pressure.

The present invention further provides a novel approach for reducing intraocular pressure associated with ocular hypertensive disorders, and thus can be useful in the prevention, management and treatment of ocular hypertension.

The method of the present invention is useful for the management and/or treatment of primary glaucoma, which consists of two types: narrow angle or acute congestive and wide angle or chronic simple glaucoma. Yet another embodiment of the present invention is the management of secondary glaucoma.

The method of the present invention is useful to enhance the effects of therapeutic agents and adjunctive agents used to treat and manage the different types of glaucoma. Therapeutic agents used to treat narrow angle or acute congestive glaucoma include, for example, physostigmine salicylate and pilocarpine nitrate. Adjunctive therapy used in the management of narrow angle glaucoma includes, for example, the intravenous administration of a carbonic anhydrase inhibitor such as acetozolamide to reduce the secretion of aqueous humor, or of an osmotic agent such as mannitol or glycerin to induce intraocular dehydration. Therapeutic agents used to manage wide angle or chronic simple glaucoma and secondary glaucoma include, for example, parasympathomimetic agents, such as pilocarpine nitrate, short-acting anticholinesterase agents such as physostigmine salicylate, long acting anticholinesterase inhibitors such as demecarium bromide, echothiophate iodide, isofluorophate, beta-adrenergic antagonists, such as timolol maleate, and sympathomimetic agents, such as epinephrine and phenylephrine. More recently, prostaglandin analogues (latanoprost (Xalatan), bimatoprost (Lumigan™)), alpha adrenergic agonists (brimonidine), and Rescula, which reduces intraocular pressure by an unknown mechanism, have been used to manage cases where glaucoma is associated with ocular hypertension.

High doses may be required for some therapeutic agents to achieve levels to effectuate the target response, but may often be associated with a greater frequency of dose-related adverse effects. Thus, combined use of the compounds of the present invention with agents commonly used to treat glaucoma allows the use of relatively lower doses of such agents resulting in a lower frequency of adverse side effects associated with long-term administration of such therapeutic agents. Thus, another indication of the compounds in this invention is to reduce adverse side effects of drugs used to treat glaucoma, such as the development of cataracts with long-acting anticholinesterase agents including demecarium, echothiophate, and isoflurophate.

The present invention provides a method of using indole derivatives of Formulae I, II, III, and IV with increased duration and/or magnitude of action in reducing intraocular pressure.

Description of Compounds

The present invention provides a method for using indole derivatives of Formulae I–IV:

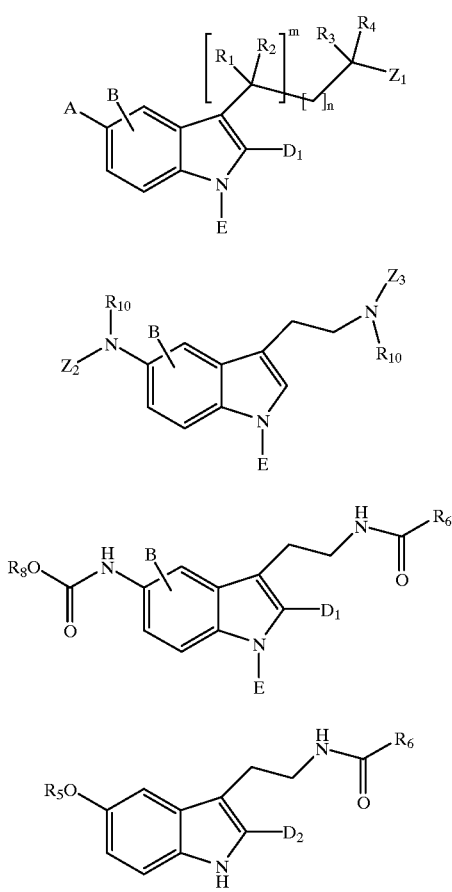

wherein:

n=0,1,2,3,4 or 5;

m=0 or 1;

$R_1$ and $R_2$ are each independently H, (un)substituted linear-, branched- or cyclo-alkyl,-alkenyl, -alkynyl, -aryl, -aralkyl, -aralkenyl, -aralkynyl, $R_6(CO)$—, F, $OR_5$; either $R_1$ or $R_2$ can be $R_6R_7N(CO)$—;

or optionally, $R_1$ and $R_2$ when taken together can represent oxo; or a (un)substituted carbocycle or heterocycle of 4,5,6, or 7 members;

$R_3$ and $R_4$ are each independently H, (un)substituted linear-, branched- or cyclo-alkyl, -alkenyl, -alkynyl, -aryl, -aralkyl, -aralkenyl, -aralkynyl, $R_6(CO)$—;

or optionally, $R_3$ and $R_4$ when taken together can represent a (un)substituted carbocycle or heterocycle of 4,5,6, or 7 members;

or optionally, $R_2$ $R_4$ when taken together can represent a (un)substituted carbocycle or heterocycle of 4, 5, 6, or 7 members;

$R_5$=H, (un)substituted linear-, branched- or cyclo-alkyl, -alkenyl, -alkynyl, -aryl, -aralkyl, aralkenyl, -aralkynyl, $R6R_7N(CO)$—, $R_6(CO)$—, $R_8O(CO)$—, $R_8S(O)_2$—, $R_8S(O)$—, $R_8OS(O)_2$—, $R_8S(O)$—, $R_6R_7NP(O)(OR_9)$—, $R_8P(O)(OR_9)$—, $(R_8O)P(O)(OR_9)$—, $CF_3$—;

$R_6$ and $R_7$ are independently H, (un)substituted linear-, branched- or cyclo-alkyl, -alkenyl, -alkynyl, -aryl, -aralkyl, -aralkenyl, -aralkynyl or heterocyclic ring;

or when optionally taken together, $NR_6R_7$ can represent a (un)substituted ring of 3, 4, 5, 6, or 7 members;

$R_8$=(un)substituted linear-, branched- or cyclo-alkyl, -alkenyl, -alkynyl, -aryl, -aralkyl, -aralkenyl, aralkynyl, heterocyclic ring or $CF_3$—;

$R_9$=H, (un)substituted linear-, branched- or cyclo-alkyl, -alkenyl, -alkynyl, -aryl, -aralkyl, aralkenyl, -aralkynyl; or optionally taken together, $R_6$ and $R_9$ can represent a ring of 5, 6, or 7 members;

$R_{10}$=H, (un)substituted linear-, branched- or cyclo-alkyl, -alkenyl, -alkynyl, -aryl, -aralkyl, aralkenyl, -aralkynyl, heterocycle, $R_6R_7N(CO)$—, $R_6(CO)$—, $R_8O(CO)$—, $R_8S(O)_2$—, $R_8OS(O)_2$—, $R_6R_7NS(O)_2$—, $CF_3$—;

$R_{11}=R_6R_7N(CO)$—, $R_6(CO)$—, $R_8O(CO)$—, $R_8S(O)_2$—, $R_8OS(O)_2$—, $R_6R_7NS(O)_2$—, $X_{1=O,S,NR_9}$, —$CF_2$—, —$CH_2$—, —$CH_2CH_2$—, —$CH_2CH_2CH_2$—, or absent;

$Z_1=OR_5$ or $NR_{10}R_{11}$;

alternatively, $D_1$ and $R_6$ are absent and the carbonyl participates in a ring bridging the two positions;

$Z_2$ and $Z_3$ are independently $R_6R_7N(CO)$—, $R_6(CO)$—, $R_8O(CO)$—, $R_8S(O)_2$—, $R_8OS(O)_2$—, $R_6R_7NS(O)_2$—;

A=halogen, $NO_2$, CN or $R_5$—$X_1$—;

B=halogen, $NO_2$, CN or $R_5$—$X_1$—;

or optionally, if B is not equal to halogen, $NO_2$, CN or H, then B taken together with $R_1$ can represent a (un)substituted carbocyclic or heterocyclic ring of 5, 6, or 7 members;

or optionally, if B is not equal to halogen, $NO_2$, CN or H, then B taken together with E (only when B is in position 7 of the indole) can represent a (un)substituted heterocyclic ring of 5, 6, or 7 members;

or optionally, B and $Z_1$ when taken together (only when B is in position 4 of the indole) can represent a (un)substituted heterocyclic ring of 5, 6, or 7 members;

or optionally, B and $R_1$ when taken together (only when B is in position 4 of the indole) can represent a (un)substituted carbocyclic or heterocyclic ring of 5, 6, or 7 members;

$D_1$=halogen, $NO_2$, CN or $R_5$—$X_1$—;

$D_2$=H, (un)substituted linear-, branched- or cyclo-alkyl, halogen, substituted or unsubstituted aryl, or substituted or unsubstituted arylalkyl;

E=H, (un)substituted linear-, branched- or cyclo-alkyl, -alkenyl, -alkynyl, -aryl, -aralkyl, aralkenyl, -aralkynyl, $R_8O(CO)$—, $R_8S(O)_2$—, or $OR_6$;

or optionally $E=R_6(CO)$—, provided that when $Z_1=NR_{10}R_{11}$, one of $R_{10}$ or $R_{11}$ is H;

or optionally $E=R_6(CO)$—, provided that when $Z_1=OR_5$, $R_5$ is not H, alkyl, aryl, or aralkyl;

or optionally $E=R_6R_7N(CO)$—, provided that when $Z_1=NR_{10}R_{11}$, one of $R_{10}$ or $R_{11}$ is H;

or optionally $E=R_6R_7N(CO)$—, provided that when $Z_1=OR_5$, $R_5$ is not H, alkyl, aryl, or aralkyl; or optionally, $D_1$ and E when taken together can represent a (un)substituted heterocyclic ring of 4, 5, 6, or 7 members;

or optionally, $D_1$ and $R_1$ when taken together can represent a (un)substituted carbocyclic or heterocyclic ring of 5, 6, or 7 members;

or optionally, $D_1$ and $R_3$ when taken together can represent a (un)substituted carbocyclic or heterocyclic ring of 5, 6, or 7 members;

or optionally, $D_1$ and $Z_1$ when taken together can represent a (un)substituted heterocyclic ring of 5, 6, or 7 members;

or optionally, $Z_1$ and $R_1$ when taken together can represent a (un)substituted heterocycle of 4, 5, 6, or 7 members;

provided that when n=0, m=1, $R_5$=$CH_3$, $X_1$=O, B=$D_1$= E=$R_3$=$R_4$=H, then Z is not —NHAc;

also provided that when $D_2$=H, and $R_5$=$CH_3$ then $R_6$ is not $CH_3$;

Enantiomers, diastereomers, cis/trans isomers, pharmaceutically useful salts, and mixtures thereof are included in this invention.

A preferred compound useful for this invention is 5-(methoxycarbonylamino)-N-acetyltryptamine (MCA-NAT), also known as GR 135531.

A preferred embodiment of the present invention relates to the compound of Formula II in which:

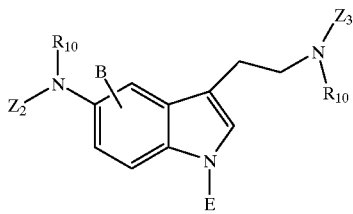

II $Z_2$ and $Z_3$ are independently $NR_6R_7$(CO)—, $R_6$(CO)—, $R_8O$(CO)—, $R_8S(O)_2$—, $R_8$ $OS(O)_2$, $NR_6R_7S(O)_2$—;

or optionally, each unit $Z_2$—N—$R_{10}$, and $Z_3$—N—$R_{10}$ can independently represent a ring of 4–7 members;

and $D_1$ of Formula I is now H.

Another preferred embodiment of the present invention relates to the compound of Formula III wherein:

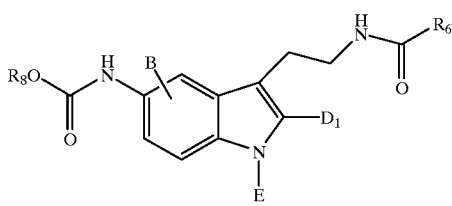

III $D_1$ is defined as in the broad embodiment, or optionally $D_1$ may form a ring with $R_6$ or in a further option $D_1$ and $R_6$ are absent with the carbonyl participating in a ring bridging the two positions; all other terms are as defined previously A more preferred embodiment of the present invention relates to the compound of Formula III wherein:

B, $D_1$, and E=H all terms are defined as previously;

Another preferred embodiment of the present invention relates to the compound of Formula IV wherein:

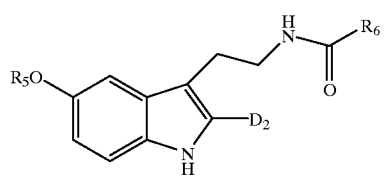

IV $D_2$=H, (un)substituted linear-, branched- or cyclo-alkyl, halogen, substituted or unsubstituted aryl, or substituted or unsubstituted arylalkyl;

Except when $R_5$=$R_6$=$CH_3$, then $D_2$ is not equal to H;

Another preferred embodiment of the present invention relates to the compound of Formula IV wherein:

$R_5$=$C_1$–$C_4$ alkyl, acetyl, formyl or $CF_3$;

$R_6$=H, $C_1$–$C_4$ alkyl, or $CF_3$;

Except when $R_5$=$CH_3$, and $D_2$=H, then $R_6$ cannot be $CH_3$.

Definitions: The expression (un)substituted relating to the terms alkyl, alkenyl, alkynyl, aryl, aralkyl, aralkenyl, aralkynyl means said group may or may not be substituted with a radical chosen from the same group or from halogen, nitrogen, oxygen, phosphorus or sulfur. The terms alkyl, alkenyl, alkynyl refer to such radicals containing from 1 to 9 carbon members. The terms aralkyl, aralkenyl, aralkynyl refer to groups with groups according to the parent definition comprised of both radicals. The term cyclo, without further specification, refers to an (un)substituted ring of from 3–7 members. The term heterocyclic means a ring containing one or more non-carbon atoms and any or no degrees of unsaturation.

Specific examples of compounds of the present invention and methods of making said compounds are provided. This invention provides a method of using a formulation of a pharmaceutical composition comprising indole derivatives melatonergic analogues of Formulae I–IV and a pharmaceutically acceptable carrier, for use in reducing intraocular pressure and thereby treating glaucoma. The compounds of the present invention also encompass their non-toxic pharmaceutically acceptable salts, such as, but not limited to, chlorides, sulfates, and acetates, as well as sodium, ammonium and pyridinium. Pharmaceutically acceptable salts are salts that retain the desired biological activity of the parent compound and do not impart undesired toxicological effects. The present invention also encompasses prodrugs of the compounds disclosed herein. Those skilled in the art will recognize various synthetic methodologies, which may be employed to prepare non-toxic pharmaceutically acceptable salts and prodrugs of the compounds.

Though the compounds of the present invention are primarily concerned with the treatment of human subjects, they may also be employed for the treatment of other mammalian subjects such as dogs and cats for veterinary purposes.

The pharmaceutical utility of compounds of this invention are indicated by the changes in IOP as measured by means of a TOPONEN contact tonometer supplied by Xomed (Jacksonville, Fla., USA). The efficacy of these compounds is reflected in their ability to activate melatonin receptors to effectuate the target response. The target response is the reduction in intraocular pressure associated with glaucoma. The effective dose will depend on characteristics of the individual patient, activity of the specific compound employed, mode of administration, and characteristics of the disease or disorder, and can be determined by those skilled in the art.

Dosage and/or concentration levels of the order of from about $10^{-12}$M to about $10^{-3}$M, preferably in the range from about $10^{-11}$M to about $10^{-4}$M, more preferably from about $10^{-10}$ to about $10^{-5}$M.

Administration of Novel Compounds

The compounds of the present invention may be administered by any means known to those skilled in the art for treatment of eye diseases. The indole derivatives are administered in a sterile preparation comprising the active compound or pharmaceutically acceptable salt thereof with a pharmaceutically acceptable vehicle or carrier therefor.

The active compounds disclosed herein may be administered to the eyes of a patient by any suitable means, but are preferably administered as a liquid or gel suspension of the active compound in the form of drops of liquid, liquid washes, sprays, ointments, or gel. Alternatively, the active compounds may be applied to the eye via liposomes or other carriers such as cyclodextrins. Further, the active compounds may be infused into the tear film via a pump-catheter system. Another embodiment of the present invention involves the active compound contained within a continuous or selective-release device, for example, membranes such as, but not limited to, those employed in the Ocusert™ System (Alza Corp., Palo Alto, Calif.). As an additional embodiment, the active compounds can be contained within, carried by, or attached to contact lenses, that are placed on the eye. Another embodiment of the present invention involves the active compound contained within a swab or sponge that can be applied to the ocular surface. Another embodiment of the present invention involves the active compound contained within a liquid spray that can be applied to the ocular surface. Another embodiment of the present invention involves an injection of the active compound directly into the lachrymal tissues or onto the eye surface, or intravitreal injection.

The topical solution containing the active compound may also contain a physiologically compatible vehicle, as those skilled in the ophthalmic art can select using conventional criteria. The vehicles may be selected from the known ophthalmic vehicles which include, but are not limited to, saline and aqueous electrolyte solutions, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

In addition to the topical method of administration described above, there are various methods of administering the active compounds of the present invention systemically such that the compounds reach the eyes via systemic absorption and circulation. One such means would involve an aerosol suspension of respirable particles comprised of the active compound, which the subject inhales. The active compound would be absorbed into the bloodstream via the lungs or contact the ocular tissues via the nasolacrimal ducts, and subsequently contact the intraocular cells in a pharmaceutically effective amount. The respirable particles may be liquid or solid, with a particle size sufficiently small to pass through the mouth and larynx upon inhalation; in general, particles ranging from about 1 to 10 microns, but more preferably 1–5 microns, in size are considered respirable.

Another means of systemically administering the active compounds to the eyes of the subject would involve administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops may be prepared by combining the active compound with a suitable vehicle, such as sterile pyrogen free water or sterile saline by techniques known to those skilled in the art.

Other means of systemic administration of the active compound would involve oral administration, in which pharmaceutical compositions containing compounds of Formulae I, II, III, and IV are in the form of tablets, lozenges, aqueous or oily suspensions, dispersible powders or granules, emulsion, hard or soft capsules, or syrups or elixirs. Compositions intended for oral use may be prepared according to any method known to the art for the manufacture of pharmaceutical compositions and such compositions may contain one or more agents selected from the group consisting of: sweetening agents, flavoring agents, coloring agents and preserving agents in order to provide pharmaceutically elegant and palatable preparations. Tablets contain the active ingredient in admixture with nontoxic pharmaceutically acceptable excipients that are suitable for the manufacture of tablets. These excipients may be, for example, inert diluents, such as calcium carbonate, sodium carbonate, lactose, calcium phosphate or sodium phosphate; granulating and disintegrating agents, for example, corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Additional means of systemic administration of the active compound to the eyes of the subject would involve a suppository form of the active compound, such that a therapeutically effective amount of the compound reaches the eyes via systemic absorption and circulation.

Further means of systemic administration of the active compound would involve direct intra-operative instillation of a gel, cream, powder, foam, crystals, liposomes, spray, or liquid suspension form of the compound, such that a therapeutically effective amount of the active compound contacts the ocular tissues of said subject via systemic absorption and circulation. The invention is illustrated further by the following examples, which are not to be construed as limiting the invention in scope of the specific procedures described in them.

EXAMPLE 1

5-Nitro-tryptamine

This procedure is adapted from the similar procedure in: Macor et. al. *Synth. Comm.* 23: 65–72 (1993))

Oxalyl chloride (19.2 mmol) is added dropwise to a suspension of 5-nitroindole (6.2 mmol) and phthalimide (0.4 g) in ether (30 mL) and the mixture stirred 48 h at 24° C. The reaction vessel is then equipped with a Dewar condenser, chilled to 0° C., and anhydrous ammonia bubbled through the mixture during 1.5 h. The gas and solvent are removed in vacuo. The resulting yellow solid is triturated with water, filtered, and the retentate washed with toluene. The solid is dried, affording 2-amino-1-(5-nitro-1H-indol-3-yl)-ethane-1,2-dione. A portion of this compound (0.59 mmol) is taken into THF (15 mL) and treated with borane-THF (2.4 mL of 1 M solution) 16 h at 28° C. The reaction is neutralized with sodium bicarbonate and extracted with ethyl acetate. The ethyl acetate extract is dried in vacuo, redissolved in ethanol (10 mL) and refluxed in the presence of cesium fluoride (360 mg) and sodium carbonate (312 mg). The mixture is filtered through Celite, evaporated and the residue chromatographed on silica gel using chloroform-methanol-ammonia (8:2:0.2) as eluent affording the title compound (20 mg).

EXAMPLE 2

N-[2-(5-Nitro-1H-indol-3-yl)-ethyl]-acetamide

5-Nitrotryptamine (6 mmol) is dissolved in pyridine (15 ml) and treated with acetic anhydride (7 mmol) 20 min at 27° C. The solvents are removed in vacuo, the residue taken into a small amount of methanol and passed through a short plug of silica with 5% methanol-chloroform eluent. Product-containing fractions are pooled, evaporated and dried thoroughly at <0.1 mm Hg.

EXAMPLE 3

N-[2-(5-Amino-1H-indol-3-yl)-ethyl]-acetamide

The product from Example 2 (0.05 mmol) is taken into ethanol (3 mL) and hydrogenated 6 h at 3 atmospheres of $H_2$ pressure over a catalytic amount of 10% Pd/C. The catalyst is removed by filtration through Celite and the solvent removed in vacuo, affording the title compound. This product is somewhat air sensitive and is used immediately for subsequent reactions.

EXAMPLE 4

{3-[2-(2-Hydroxy-benzylamino)-ethyl]-1H-indol-5-yl}-carbamic Acid Methyl Ester

5-Nitrotryptamine (6 mmol) and salicylaldehyde (7 mmol) are dissolved in ethanol (35 mL) buffered with potassium hydroxide (0.15 g) and treated with sodium borohydride (18 mmol) 8 h at 24° C. The ethanol is removed in vacuo and the residue partitioned between ether and water, the ether phase dried, evaporated and the oil chromatographed on silica gel with ethyl acetate-hexane to afford 2-{[2-(5-nitro-1H-indol-3-yl)-ethylamino]-methyl}-phenol. After hydrogenation over Pd/C as above, the residue is dissolved in pyridine (12 mL) and treated with methyl chloroformate (9 mmol). A brownish precipitate forms immediately upon addition of the chloroformate, which dissolves during 20 min. After a short time silica gel TLC (5% methanol-chloroform eluent) is performed to judge completion of the reaction. The mixture is evaporated to dryness and maintained at a vacuum of <0.1 mmHg at least 2 h. It is then dissolved in a small amount of methanol, and purified by reverse-phase HPLC with a gradient of water to methanol.

EXAMPLE 5

[3-(2-Propionylamino-ethyl)-1H-indol-5-yl]-carbamic Acid Methyl Ester

5-Nitro-tryptamine (6 mmol) is dissolved in pyridine (15 ml) and treated with propionic anhydride (7 mmol) 20 min at 27° C. The solvents are removed in vacuo and the residue dried thoroughly at <0.1 mm Hg. The residue is then hydrogenated and transformed to the carbamic acid methyl ester as in the previous example. The title compound is purified by filtration through a short plug of silica gel with 5% methanol-chloroform as eluent.

EXAMPLE 6

N-[2-(5-Dimethylamino-1H-indol-3-yl)-ethyl]-acetamide

N-[2-(5-Nitro-1H-indol-3-yl)-ethyl]-acetamide (0.6 mmol) is taken into acetonitrile (1 mL) and stirred with a catalytic amount of DMAP and di-t-butyl dicarbonate (0.7 mmol) for 1 h. The solvent is removed in vacuo and the remaining oil chromatographed with ethyl acetate-hexane as eluent. The product is dissolved in ethanol (10 ml) and hydrogenated as above. The residue is dissolved in DMF (2 mL), and diisopropylethylamine (1.4 mmol) followed by methyl iodide (1.4 mmol) added. The mixture is stirred 3 h at 25° C. then filtered, evaporated to dryness, dissolved in ethanol and decolorized with activated charcoal. The residue is dissolved in trifluoroacetic acid with 1 equivalent of thiophenol and stirred 1 h at 20° C. The solvent is removed, the compound dissolved in isopropanol-water (5:1) and treated with 2 equivalents (w/w) of Dowex AG1-X8 ion exchange resin in the hydroxide form. Evaporation of the solvent followed by crystallization affords the title compound.

EXAMPLE 7

[3-(2-Acetylamino-ethyl)-2-phenyl-1H-indol-5-yl]-carbamic acid methyl ester

2-[2-(5-Nitro-1H-indol-3-yl)-ethyl]-isoindole-1,3-dione (1 mmol) is dissolved in THF/chloroform (1:1) and treated with pyridine hydrobromide perbromide at 0° C. for 90 min, then eluted from a silica column with chloroform-methanol. The product is dissolved in toluene-ethanol (1:1) and treated with phenylboronic acid (1.5 equiv), sodium carbonate (2.5 equiv), lithium chloride (3 equiv), and palladium tetrakis (triphenylphosphine) (5 mol %). The mixture is refluxed 4 h, concentrated in vacuo, and the oil chromatographed on silica eluted with ethyl acetate-hexane to afford 2-[2-(5-nitro-2-phenyl-1H-indol-3-yl)-ethyl]-isoindole-1,3-dione. This compound is dissolved in ethanol (6 mL) and refluxed with ethylenediamine (3 equiv) 18 h. The solvent is removed in vacuo and the material acetylated with pyridine-acetic anhydride (1:1, 6 mL). The solvent is removed in vacuo and the residue chromatographed on silica eluted with ethyl acetate-hexane. This product is hydrogenated and transformed to the carbamic acid methyl ester as in the example above. Purified product is isolated by reverse-phase HPLC.

EXAMPLE 8

[3-(2-Acetylamino-ethyl)-2-methyl-1H-indol-5-yl]-carbamic Acid Methyl Ester

Oxalyl chloride (4.4 mmol) is added dropwise to a suspension of 2-methyl-5-nitroindole (1.4 mmol) and phthalimide (0.1 g) in ether (10 mL) and the mixture stirred 48 h at 24° C. The reaction vessel is then equipped with a Dewar condenser, chilled to 0° C., and anhydrous ammonia bubbled through the mixture during 1.5 h. The gas and solvent are removed in vacuo. The resulting tan solid is triturated with water, filtered, and the retentate washed with toluene. The solid is dried, affording (2-amino)-1-(5-nitro-1H-indol-3- yl)-ethane-1,2-dione. A portion of this compound (0.59 mmol is taken into THF (15 mL) and treated with borane-THF (2.4 mL of 1 M solution) 16 h at 28° C. The reaction is neutralized with sodium bicarbonate and extracted with ethyl acetate. The ethyl acetate extract is dried in vacuo, redissolved in ethanol (10 mL) and refluxed in the presence of cesium fluoride (360 mg) and sodium carbonate (312 mg). The mixture is filtered through Celite, evaporated and the residue chromatographed on silica gel using chloroform-methanol-ammonia (8:2:0.2) as eluent affording 2-(2-methyl-5-nitro-1H-indol-3-yl)-ethylamine. This compound is acetylated, hydrogenated and transformed to the carbamic acid methyl ester as above.

EXAMPLE 9

[3-(3-Acetylamino-prop-1-yl)-1H-indol-5-yl]-carbamic Acid Methyl Ester

Diethyl cyanomethane phosphonate (7 mmol) in THF-HMPA (9:3, 11 mL) at 0° C. is treated with sodium hydride (7 mmol) for 10 min. 1-acetyl-5-nitroindole-3-carboxaldehyde (6 mmol) is next added and the solution stirred at room temperature for 3 h. The mixture is poured into ice-water and the pH adjusted to 5. Evaporation of the solvent and trituration of the residue with methanol affords 3-(1-acetyl-5-nitro-1H-indol-3-yl)-propenitrile as a solid. This is taken into ethanol saturated with ammonia (75 mL) and hydrogenated over Raney nickel 16 h at 3 atmospheres $H_2$ pressure. Removal of the catalyst followed by acetylation as above produces N-[3-(5-nitro-1H-indol-3-yl)-prop-1-yl]-acetamide which is hydrogenated, carbamoylated, and purified by reverse-phase HPLC as above.

EXAMPLE 10

[3-(3-Benzenesulfonylamino-ethyl)-1H-indol-5-yl]-carbamic Acid Methyl Ester

5-Nitrotryptamine (6 mmol) is dissolved in pyridine (15 ml) and treated with benzenesulfonyl chloride for 4 h at 25° C. The mixture is poured into ice-water and extracted with ether (3×50 mL). The ether extracts are washed with 1 M HCl (2×50 mL) then with saturated sodium bicarbonate (2×50 mL), dried with magnesium sulfate and evaporated at reduced pressure. The resulting solid is hydrogenated and transformed to the carbamic acid methyl ester as in the previous examples.

EXAMPLE 11

N-[2-(5- Ureido-1H-indol-3-yl)-ethyl]-acetamide

The product from Example 3 is dissolved in acetic acid-water (1:2, 3 mL) and sodium cyanate (2 mmol) added. This is stirred until a brownish gum is precipitated. The mixture is extracted with chloroform (3×30 mL), and the organic extracts washed with saturated sodium bicarbonate, dried with magnesium sulfate and the solvent evaporated in vacuo. The resulting product is purified by reverse-phase HPLC as above.

EXAMPLE 12

N-[2-(5-Methoxycarbonylamino-1H-indol-3-yl)-ethyl]-succinamic Acid

Triethylamine (12 mmol), DMAP (0.6 mmol), and succinic anhydride (9 mmol) are added to a solution of 5-nitrotryptamine (6 mmol) in dichloromethane (25 mL). The mixture is stirred 4 h, the solvent removed in vacuo, and the residue chromatographed on silica gel using 10% methanol-chloroform with 1% acetic acid as eluent. The product is then hydrogenated and transformed to the carbamic acid methyl ester as in the previous examples. Purified product is obtained by reverse-phase HPLC as above.

EXAMPLE 13

[3-(2-Acetylamino-ethyl)-1H-indol-5-yl]-carbamic Acid Allyl Ester

The product from example 3 (5 mmol) is then treated with allyl chloroformate in the same manner as above, and purified on silica gel with 5% methanol in chloroform as eluent.

EXAMPLE 14

[3-(2-Acetylamino-ethyl)-1H-indol-5-yl]-carbamic acid 3-hydroxy-prop-1 -yl Ester

[3-(2-Acetylamino-ethyl)-1H-indol-5-yl]-carbamic acid allyl ester (1 mmol) is dissolved in THF (27 mL) and borane-THF (2 mmol) added dropwise. After 2 h, sodium hydroxide (4 mL of 3 M) and hydrogen peroxide (4 mL of 30%) are added and the solution stirred an additional 1 h. The solution is concentrated to half its volume, 10 mL water is added and it is extracted with ethyl acetate (4×25 mL). The combined extracts are washed with brine, dried, the solvent removed in vacuo, and the product chromatographed on silica gel with 5% methanol in chloroform as eluent.

EXAMPLE 15

[3-(2-Acetylamino-ethyl)-1H-indol-5-yl]-carbamic acid 2,3-dihydroxy-allyl Ester

[3-(2-Acetylamino-ethyl)-1H-indol-5-yl]-carbamic acid allyl ester (1 mmol) is dissolved in pyridine (7 mL) and treated with osmium tetraoxide (0.01 mmol) and $H_2O_2$ (1 mL of a 30% aqueous solution) 15 h at 25° C. The solvents are removed in vacuo and the product chromatographed on silica gel with 10% methanol in chloroform as eluent.

EXAMPLE 16

N-[3-(2-Acetylamino-ethyl)-1H-indol-5-yl]-acetamide

The product from Example 1 (0.05 mmol) is taken into ethanol (3 mL) and hydrogenated overnight at 3 atmospheres of $H_2$ pressure with a catalytic amount of 10% Pd/C. The catalyst is removed by filtration through Celite and the solvent removed in vacuo. Acetylation with pyridine/acetic anhydride as above produces the title compound.

EXAMPLE 17

[3-(2-Acetylamino-ethyl)-2-bromo-1H-indol-5-yl]-carbamic Acid Methyl Ester

A solution of 5-methoxycarbonylamino-N-acetyltryptamine (0.05 mmol) in acetic acid (0.5 mL) is treated with N-bromosuccinimide (0.05 mmol) 3.5 h at 25° C. The solution is next neutralized with 50% sodium hydroxide solution and extracted with ethyl acetate. The organic extract is evaporated and the purified product obtained following chromatography on silica gel with 2% methanol-chloroform as eluent.

EXAMPLE 18

[3-(2-Acetylamino-ethyl)-1-benzyl-1H-indol-5-yl]-carbamic acid methyl ester

Sodium hydride (0.1 mmol) is added to the product from Example 2 (0.04 mmol) in DMF (0.7 mL). The mixture immediately changes from yellow to red. After stirring 20 minutes, benzyl bromide (0.1 mmol) is added and the mixture stirred an additional 2 hours. The reaction is then partitioned between water and ethyl acetate, the layers are separated, the ethyl acetate phase removed in vacuo, and the product dried under high vacuum. The residue is then dissolved in a small amount of methanol, and the product isolated by reverse-phase HPLC with a gradient of water to methanol. This product is transformed into the title compound by hydrogenation and conversion to the carbamic acid methyl ester as in the previous examples.

EXAMPLE 19

(1-Oxo-2,3,4,9-tetrahydro-1H-βcarbolin-6-yl)-carbamic Acid Methyl Ester

A sample of 6-Nitro-2,3,4,9-tetrahydro-βcarbolin-1-one (0.05 mmol) is transformed to the title compound by hydrogenation and conversion to the carbamic acid methyl ester as in the previous examples.

EXAMPLE 20

[3-(2-Acetylamino-ethyl)-1-methyl-1H-indol-5-yl]-methyl-carbamic Acid Methyl Ester Sodium hydride (0.1 mmol) is added to a solution of 5-(methoxycarbonylamino)-N-acetyltryptamine (0.03 mmol) in DMF (0.7 mL) and the mixture stirred 20 minutes at room temperature. Iodomethane (0.1 mmol) is then added and the mixture stirred an additonal 2 hours. The reaction mixture is partitioned between water and ethyl acetate, the ethyl acetate phase removed in vacuo, and the product dried under high vacuum. The residue is then dissolved in a small amount of methanol, and the product isolated by reverse-phase HPLC with a gradient of water to methanol. This product is transformed to the title compound by hydrogenation and conversion to the carbamic acid methyl ester as in the previous examples.

EXAMPLE 21

[3-(2-Acetylamino-ethyl)-4-(1-methoxy-ethyl)-1-methyl-1H-indol-5-yl]-carbamic Acid Methyl Ester Sodium hydride (10 mmol) is added to 1-(1H-Indole-4-yl)-ethanol(4 mmol) in DMF (7 mL). After stirring 20 minutes, iodomethane (10 mmol) is added and the mixture stirred an additional 2 hours. The reaction is then partitioned between water and ethyl acetate, the layers are separated, the ethyl acetate phase removed in vacuo, and the product dried under high vacuum. The residue is then dissolved in a small amount of alcohol, and 4-(1-methoxy-ethyl)-1-methyl-1H-indole isolated by chromatography on silica gel using chloroform-methanol as eluent. This product (2 mmol) is dissolved in ether (40 mL), oxalyl chloride (8 mmol) added dropwise and the mixture stirred 8 h at 24° C. The reaction vessel is then equipped with a Dewar condenser, chilled to 0° C., and anhydrous ammonia bubbled through the mixture during 1.5 h. The gas and solvent are removed in vacuo. The resulting solid is dissolved in ethyl acetate, extracted with brine, and the ethyl acetate phase dried with magnesium sulfate and evaporated. The material is dissolved in THF (15 mL) and treated with borane-THF (3 mL of 1 M solution) 16 h at 25° C. The reaction is neutralized with sodium bicarbonate and extracted with ethyl acetate. The ethyl acetate extract is next dried in vacuc, redissolved in ethanol (10 mL) and refluxed in the presence of cesium fluoride (380 mg) and sodium carbonate (350 mg). The mixture is filtered through Celite, evaporated and the residue chromatographed on silica gel using chloroform-methanol-ammonia (9:1:0.1) as eluent affording 2-[4-(1-methoxy-ethyl)-1-methyl-1H-indol-3-yl]-ethylamine. This material is dissolved in pyridine (6 mL) and treated with acetic anhydride (3 mL) to provide N-{2-[4-(1-methoxy-ethyl)-1-methyl-1H-indol-3-yl]ethyl}-acetamide. After drying 24 h at <0.1 mmHg, the compound (1 mmol) is taken into dichloromethane (2 mL). Ammonium nitrate (1.7 mmol) is added followed by trifluoroacetic anhydride (3 mmol)). The mixture is stirred overnight, then partitioned between cold, saturated sodium bicarbonate and chloroform. The organic phase is washed with water, dried with magnesium sulfate and evaporated to dryness. The N-{2-[4-(1-methoxy-ethyl)-1-methyl-5-nitro-1H-indol-3-yl]-ethyl}-acetamide is isolated by chromatography on silica gel using ethyl acetate-hexane as eluent, and finally transformed into the title compound by hydrogenation and formation of the methyl carbamate as described in previous examples.

EXAMPLE 22

Effects of Melatonin and 5-methoxycarbonylamino-N-acetyltryptamine (5-MCA-NAT) on Intraocular Pressure in Rabbits The actions of melatonin and 5-methoxycarbonylamino-N-acetyltryptamine(5-MCA-NAT), also known as GR 135531 on intraocular pressure (IOP) were assessed in New Zealand white rabbits.

Intraocular Pressure Measurements

IOP was measured using a TONOPEN contact tonometer supplied by Xomed (Jacksonville, Fla., USA). Ten microliters of the agents were applied topically and unilaterally to the cornea, whereas the contralateral eye received the same volume of saline solution. The corneas were anesthetized to avoid any discomfort associated with the use of the tonometer. Two measurements were made before application of the agents.

Pharmacological Studies

Melatonin (Sigma, St. Louis) and 5-MCA-NAT (Tocris, Bristol, UK) were prepared in 10–100 fold higher concentrations in DMSO and diluted in saline. Doses ranging from 10 pg/10 μL to 1 mg/10 μL were applied (equivalent to 43 fmol to 43 μmol for melatonin and equivalent to 34 fmol to 34 μmol for 5-MCA-NAT) and intraocular pressure was measured at 0.5, 1, 2, 3, 4, 5, and 6 hours after the application. A single dose was tested in a single animal on a single day. The non-specific melatonin antagonist luzindole was added 30 min before the application of either melatonin or 5-MCA-NAT at a dose of 100 μg/10 uL or 342 nM.

Effect of Melatonin and 5-MCA-NAT on Rabbit IOP

Figure 2:
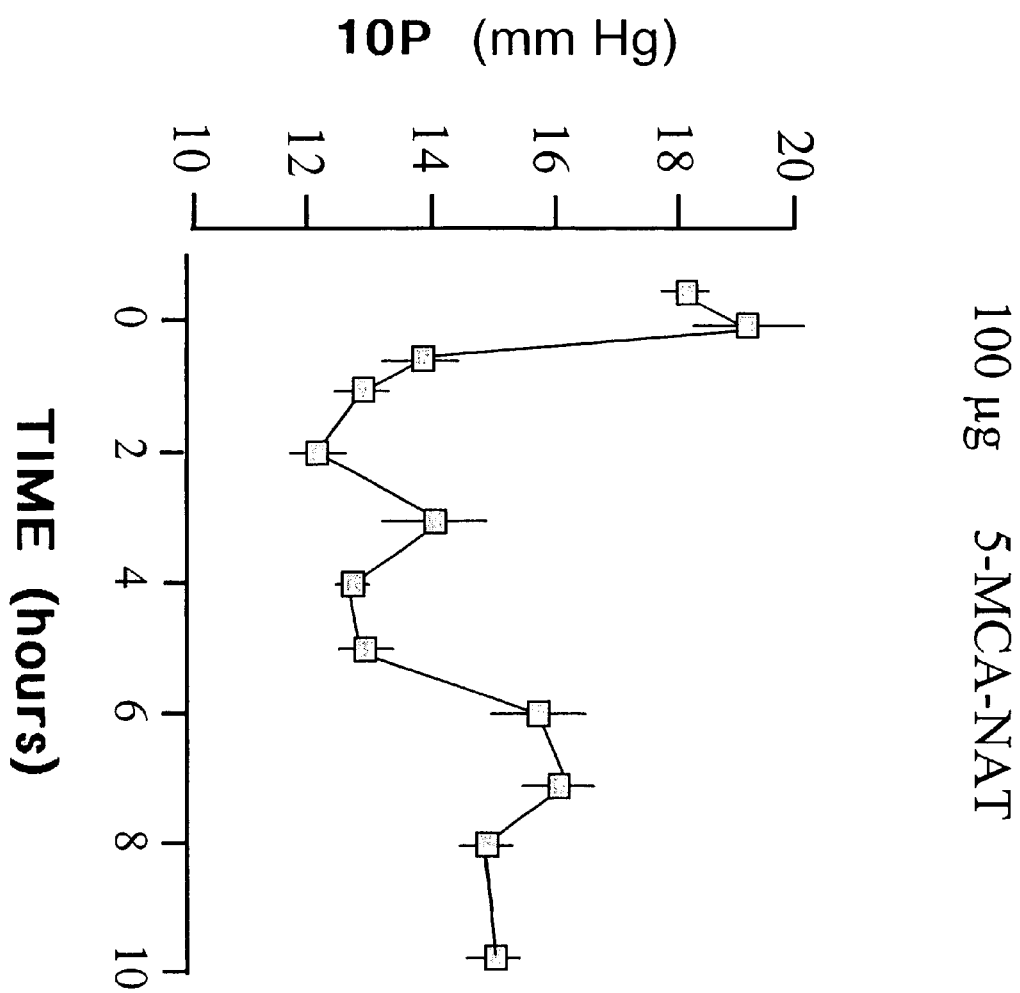
FIG. 2 illustrates the effect of an equivalent amount of 5-MCA-NAT, during 10 hours.
Figure 3:
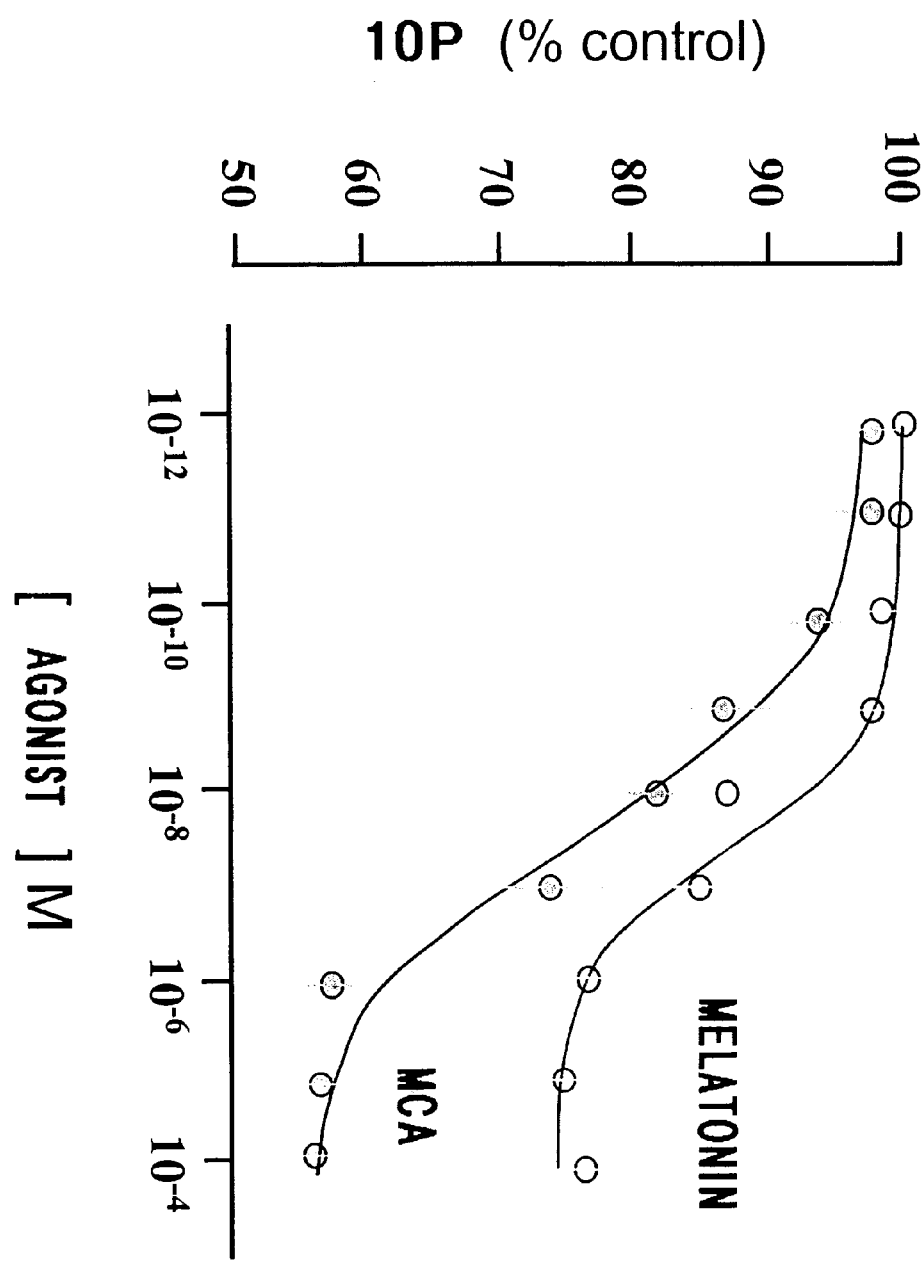
FIG. 3 compares the dose-response of 5-MCA-NAT and melatonin for lowering IOP.

Melatonin and 5-MCA-NAT (10 pg/10 μL to 1 mg/10 μL) produced a dose-dependent decrease in IOP which was maximal at 10 μg/10 μL, with a reduction of 24±4.4%(n=8). The maximal effect was observed after 1 hour and persisted during 3 hours (FIG. 1). 5-MCA-NAT (10 pg/10 μL to 1 mg/10 μL) also produced a dose-dependent decrease in IOP, which was maximal at 100 pg/10 μL, being a reduction of 43.1±3.65% (n=8). The maximal effect was observed after 2 hour and persisted during 10 hours (FIG. 2). The maximum response to 5-MCA-NAT was statistically significantly greater than that due to melatonin. The $IC_{50}$ values for melatonin and 5-MCA-NAT were 363±23.0 ng/10 μL and 423±30 ng/μL, respectively which are equivalent to doses of 1.6±0.1 nmol and 1.8±0.1 nmol, respectively (FIG. 3). These values are not significantly different from each other.

Figure 4:
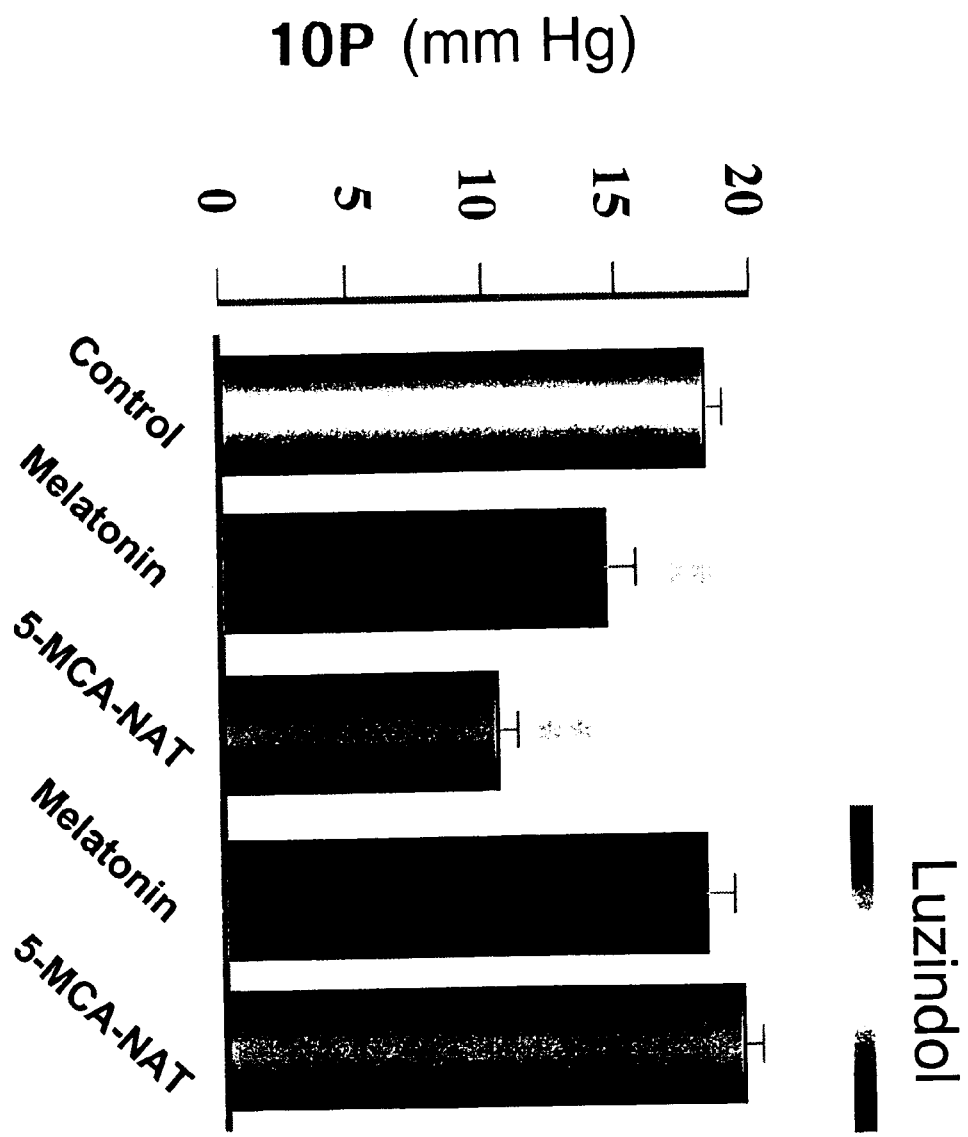
FIG. 4 illustrates reversal of the IOP-lowering effect of 5-MCA-NAT and melatonin by the melatonin receptor antagonist luzindole.

Pretreatment with non-specific melatonin receptor antagonist, luzindole (100 μg/10 μL), abolished the effect of both melatonin and 5-MCA-NAT (FIG. 4), but had no effect over a duration of six hours when applied alone.

The results show that both melatonin and the selective $MT_3$ receptor agonist 5-MCA-NAT cause dose-dependent decreases in IOP, with 5-MCA-NAT evoking a maximal response that is almost twice that of melatonin. These results suggest that assuming that there is a single population of melatonin receptors, melatonin seems to be acting as a partial agonist, whereas 5-MCA-NAT acts as a full agonist. The ability of the non-specific melatonin receptor antagonist luzindole to abolish the effects of melatonin and 5-MCA-NAT suggest that the actions of melatonin and 5-MCA-NAT are mediated through melatonin receptors.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A method of reducing intraocular pressure in a subject in need thereof, said method comprising:

administering to said subject an indole derivative in an amount effective to reduce intraocular pressure, wherein said indole derivative is a compound of Formula I:

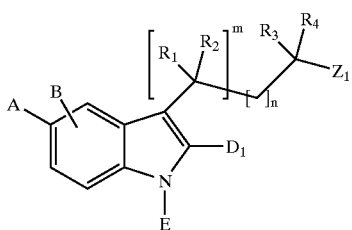

wherein:

n=0, 1, 2, 3, 4, or 5;

m=0 or 1;

$R_1$ and $R_2$ are each independently H, substituted or unsubstituted linear-, branched- or cyclo-alkyl, -alkenyl, -alkynyl, -aryl, -aralkyl, -aralkenyl, -aralkynyl, $R_6(CO)$—, F, $OR_5$, or either $R_1$ or $R_2$ is $R_6R_7N(CO)$—; or $R_1$ and $R_2$ when taken together is oxo; or a substituted or unsubstituted carbocycle, or heterocycle of 4, 5, 6, or 7 members;

$R_3$ and $R_4$ are each independently H, substituted or unsubstituted linear-, branched- or cyclo-alkyl, -alkenyl, -alkynyl, -aryl, -aralkyl, -aralkenyl, -aralkynyl, $R_6(CO)$-, or $R_3$ and $R_4$ when taken together is oxo; or a substituted or unsubstituted carbocycle or a heterocycle of 4, 5, 6, or 7 members;

or $R_2$ and $R_4$ when taken together represent a substituted or unsubstituted carbocycle or heterocycle of 4, 5, 6, or 7 members;

A=, $NO_2$, CN or $R_5$—$X_1$—;

B=halogen, $NO_2$, CN, H, or $R_5$-$X_1$-;

when B is not equal to halogen, $NO_2$, CN or H, then B taken together with $R_1$ represent a substituted or unsubstituted carbocyclic or heterocyclic ring of 5, 6, or 7 members;

when B is not equal to halogen, $NO_2$, CN or H, and when B is in position 7 of the indole, then B optionally taken together with E represent a substituted or unsubstituted heterocyclic ring of 5, 6, or 7 members;

$X_1$=O, S, $NR_9$, —$CF_2$—, —$CH_2$—, —$CH_2CH_2$-, -CH2CH2CH2-, or absent;

$R_5$=H, substituted or unsubstituted linear-, branched- or cyclo-alkyl, -alkenyl, -alkynyl, -aryl, -aralkyl, -aralkenyl, -aralkynyl, $R_6R_7N(CO)$—, $R_6(CO)$—, $R_8O(CO)$—, $R_8S(O)_2$—, $R_8S(O)$—, $R_8OS(O)_2$—, $R_8S(O)$—, $R_6R_7NS(O)_2$—, $R_6R_7NP(O)(OR_9)$—, $R_8P(O)(OR_9)$—, $(R_8O)P(O)(OR_9)$—, or $CF_3$—;

provided that when E=H, $D_1$=$R_5$—$X_1$ and $X_1$=O, or —$CH_2$—, or —$CH_2CH_2$—, or—$CH_2CH_2CH_2$—, then $R_5$ is not H, or aryl;

$R_6$ and $R_7$ are independently H, substituted or unsubstituted linear-, branched- or cyclo-alkyl, -alkenyl, -alkynyl, -aryl, -aralkyl, -aralkenyl, -aralkynyl or heterocyclic ring; when taken together, $NR_6R_7$ represent a substituted or unsubstituted ring of 3, 4, 5, 6, or 7 members;

$R_8$=substituted or unsubstituted linear-, branched- or cyclo-alkyl, -alkenyl, -alkynyl, aryl, -aralkyl, -aralkenyl, -aralkynyl, heterocyclic ring or $CF_3$—;

$R_9$=H, substituted or unsubstituted linear-, branched- or cyclo-alkyl, -alkenyl, -alkynyl, aryl, -aralkyl, -aralkenyl, -aralkynyl;

when taken together, $R_6$ and $R_9$ represent a ring of 5, 6, or 7 members;

when B is in position 4 of the indole, B and $Z_1$ taken together represent a substituted or unsubstituted heterocyclic ring of 5, 6, or 7 members;

when B is in position 4 of the indole B and $R_1$ taken together) represent a substituted or unsubstituted carbocyclic or heterocyclic ring of 5, 6, or 7 members;

E=H, substituted or unsubstituted linear-, branched- or cyclo-alkyl, -alkenyl, -alkynyl, aryl, -aralkyl, -aralkenyl, -aralkynyl, $R_8O(CO)$—, $R_8S(O)_2$—, or $OR_6$;

or E=$R_6(CO)$—, provided that when $Z_1$=$NR_{10}R_{11}$, one of $R_{10}$ or $R_{11}$ is H;

or E=$R_6(CO)$—, provided that when $Z_1$=$OR_5$, $R_5$ is not H, alkyl, aryl, or aralkyl;

or E=$R_6R_7N(CO)$—, provided that when $Z_1$=$NR_{10}R_{11}$, one of $R_{10}$ or $R_{11}$ is H;

or E=$R_6R_7N(CO)$—, provided that when $Z_1$=$OR_5$, $R_5$ is not H, alkyl, aryl, or aralkyl;

$D_1$=halogen, $NO_2$, CN or $R_5$—$X_1$—;

$D_1$ and E when taken together represent a substituted or unsubstituted heterocyclic ring of 4, 5, 6, or 7 members;

$D_1$ and $R_1$ when taken together represent a substituted or unsubstituted carbocyclic or heterocyclic ring of 5, 6, or 7 members;

$D_1$ and $R_3$ when taken together represent a substituted or unsubstituted carbocyclic or heterocyclic ring of 5, 6, or 7 members;

$D_1$ and $Z_1$ when taken together represent a substituted or unsubstituted heterocyclic ring of 5, 6, or 7 members;

$Z_1$=$OR_5$ or $NR_{10}R_{11}$;

$Z_1$ and $R_1$ when taken together represent a substituted or unsubstituted heterocycle of 4, 5, 6, or 7 members;

$R_{10}$=H, substituted or unsubstituted linear-, branched- or cyclo-alkyl, -alkenyl, -alkynyl, aryl, -aralkyl, -aralkenyl, -aralkynyl, heterocycle, $R_6R_7N(CO)$—, $R_6(CO)$—, $R_8O(CO)$—, $R_8S(O)_2$—, $R_8OS(O)_2$—, $R_6R_7NS(O)_2$—, $CF_3$—; and $R_{11}$=$NR_6R_7(CO)$—, $R_6(CO)$—, $R_8O(CO)$—, $R_8S(O)_2$—, $R_8OS(O)_2$—, $R_6R_7NS(O)_2$—;

alternatively, $D_1$ and $R_6$ are absent and the carbonyl participates in a ring bridging the two positions; provided that when n=0, m=1, $R_5$=$CH_3$, $X_1$=O, B=$D_1$=E=$R_3$=$R_4$=H, then Z is not —NHAc.

2. The method according to claim 1, wherein said indole is a compound of Formula II:

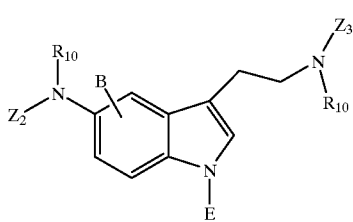

II wherein $Z_2$ and $Z_3$ are independently $R_6R_7N(CO)$—, $R_6(CO)$—, $R_8O(CO)$—, $R_8S(O)_2$—, $R_8OS(O)_2$—, $R_6R_7NS(O)_2$—; or each unit $Z_2$—N—$R_{10}$, and $Z_3$—N—$R_{10}$ independently represent a ring of 4–7 members.

3. The method according to claim 1, wherein said indole is a compound of Formula III:

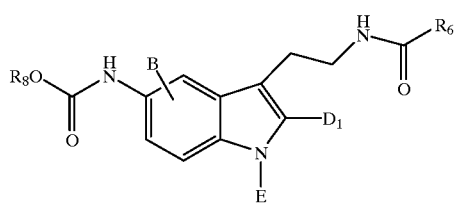

III wherein $D_1$ is defined as in claim 1 or alternately $D_1$ forms a ring with $R_6$, or alternately $D_1$ and $R_6$ are absent and the carbonyl participates in a ring bridging the two positions.

4. The method according to claim 3 wherein B=D1=E=H.

5. The method according to claim 1, wherein said indole is a compound of Formula IV:

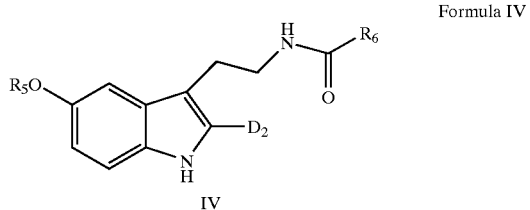

Formula IV $D_2$=H, substituted or unsubstituted linear-, branched- or cyclo-alkyl, halogen, substituted or unsubstituted phenyl, or substituted or unsubstituted arylalkyl; provided when $R_5$=$R_6$=$CH_3$, then $D_2$ is not equal to H.

6. The method according to claim 5 wherein $R_5$=$C_1$–$C_4$ alkyl, acetyl, formyl or $CF_3$; $R_6$=H, $C_1$–$C_4$ alkyl, or $CF_3$; provided when $R_5$=$CH_3$, then $R_6$ is not $CH_3$.

7. The method according to claim 1, wherein said compound is administered in an amount effective to achieve a concentration thereof on the ocular surface of said subject of from about $10^{-12}$M to $10^{-3}$M.

8. The method according to claim 1, wherein said compound is 5-methoxycarbonylamino-N-acetyltryptamine.

9. The method according to claim 1, wherein said indole is selected from the group of compounds consisting of N-[2-(5-Dimethylamino-1H-indol-3-yl)-ethyl]-acetamide, {3-[2-(2-Hydroxy-benzylamino)-ethyl]-1H-indol-5-yl}-carbamic acid methyl ester, [3-(2-Acetylamino-ethyl)-2-phenyl-1H-indol-5-yl]-carbamic acid methyl ester, [3-(2-Acetylamino-ethyl)-1-methyl-1H-indol-5-yl]-carbamic acid methyl ester, [3-(3-Acetylamino-propyl)-1H-indol-5-yl]-carbamic acid methyl ester, [3-(3-Benzenesulfonylamino-propyl)-1H-indol-5-yl]-carbamic acid methyl ester, N-[2-(5-Ureido-1H-indol-3-yl)-ethyl]-acetamide, [3-(2-Propionylamino-ethyl)-1H-indol-5-yl]-carbamic acid methyl ester, N-[2-(5-Methoxycarbonylamino- 1H-indol-3yl)-ethyl]-succinamic acid, [3-(2-Acetylamino-ethyl)-1H-indol-5-yl]-carbamic acid allyl ester, [3-(2-Acetylamino-ethyl)-1H-indol-5-yl]-carbamic acid 3-hydroxy-propyl ester, [3-(2-Acetylamino-ethyl)-1H-indol-5-yl]-carbamic acid 2,3-dihydroxy-allyl ester, and N-[3-(2-Acetylamino-ethyl)-1H-indol-5-yl]-acetamide, [3-(2-Acetylamino-ethyl)-2-bromo-1H-indol-5-yl]-carbamic acid methyl ester, [3-(2-Acetylamino-ethyl)-2-methyl-1H-indol-5-yl]-carbamic acid methyl ester, [3-(2-Acetylamino-ethyl)-1-benzyl-1H-indol-5-yl]-carbamic acid methyl ester, (1-Oxo-2,3,4,9-tetrahydro-1H-β-carbolin-6-yl)- carbamic acid methyl ester, and [3-(2-Acetylamino-ethyl)-4-(1-methoxy-ethyl)-1-methyl-1H-indol-5-yl]-carbamic acid methyl ester.

10. The method according to claim 1, wherein said indole derivative of Formula I is administered to a subject in need of treatment, to treat a condition selected from the group consisting of ocular hypertension and glaucoma, in and amount effective to treat said condition.

11. The method according to claim 10, wherein said glaucoma is primary glaucoma.

12. The method according to claim 11, wherein said primary glaucoma is selected from the group consisting of narrow-angle, acute congestive glaucoma; wide-angle, chronic simple glaucoma; and secondary glaucoma.

13. The method according to claim 12, wherein said indole derivative is co-administered with therapeutic and adjunctive agents used to manage narrow angle, acute congestive glaucoma, selected from the group consisting of: anticholinesterase inhibitors, carbonic anhydrase inhibitors, prostaglandin analogues, and osmotic agents.

14. The method according to of claim 13, wherein said anticholinesterase inhibitor is salicylate or pilocarpine nitrate; said carbonic anhydrase inhibitor is acetazolamide; said prostaglandin analogue is Xalatan or bimatoprost; and said osmotic agent is mannitol or glycerin.

15. The method according to claim 1, wherein said indole is co-administered with therapeutic agents used to manage wide angle, chronic simple glaucoma, and is selected from the group consisting of parasympathomimetic agents, short-acting anticholinesterase agents, long-acting anticholinesterase agents, alpha-adrenergic agonists, beta-adrenergic antagonists, sympathomimetic agents, and prostaglandin analogues.

16. The method according to claim 15, wherein said parasympathomimetic agent is pilocarpine nitrate; said short-acting anticholinesterase inhibitor is physostigmine salicylate; said long-acting anticholinesterase inhibitor is demecarium bromide, echothiophate iodide or isofluorophate; said beta adrenergic antagonist is timolol maleate; said sympathomimetic agent is epinephrine or phenylephrine; and said prostaglandin analogue is latanoprost or bimatoprost.

17. The method according to claim 12, wherein said indole derivative is co-administered with therapeutic agents used to manage secondary glaucoma, and selected from the group consisting of: parasympathomimetic agents, short-acting anticholinesterase agents, long-acting anticholinesterase agents, beta-adrenergic antagonists, sympathomimetic agents, and prostaglandin analogues.

18. The method according to claim 17, wherein said parasympathomimetic agent is pilocarpine nitrate; said short-acting anticholinesterase inhibitor is physostigmine salicylate; said long-acting anticholinesterase inhibitor is demecarium bromide, echothiophate iodide or isofluorophate; said beta adrenergic antagonist is timolol maleate; said sympathomimetic agents is epinephrine or phenylephrine; and said prostaglandin analogue is latanoprost or bimatoprost.

19. The method according to claim 1, wherein said indole derivative is administered in a sterile preparation comprising said compound or pharmaceutically acceptable salts thereof together with a pharmaceutically acceptable vehicle or carrier therefor.

20. The method according to claim 19, wherein said pharmaceutically acceptable carrier is a physiologically compatible vehicle selected from the group consisting of: aqueous electrolyte solutions, polyethers, polyvinyls, polymers of acrylic acid, lanolin, and glucosaminoglycans, whereby said formulation enhances outflow of fluid from the eye and thereby reduces intraocular pressure.

21. The method according to claim 1, wherein said method of administering said compound is selected from the group consisting of a) topical administration via a carrier vehicle selected from a group consisting of, drops of liquid, liquid wash, gels, ointments, sprays and liposomes; b) infusion to said ocular surface via a device selected from a group consisting of, a pump-catheter system, a continuous or selective release device, and a contact lens; and c) systemic administration.

22. The method according to claim 21, wherein said systemic administration of said indole is accomplished by administering an intra-operative instillation of a gel, cream, powder, foam, crystals, liposomes, spray, drops of liquid, or liquid suspension form of said compound, such that a therapeutically effective amount of said compound contacts the ocular tissues of said subject via systemic absorption and circulation.

23. The method according to claim 1, wherein said indole derivative is used to reduce adverse side effects of drugs used to treat glaucoma, comprising the step of:
    administering said indole derivative with a drug selected from the group consisting of: demecarium, echothiophate and isofluorophate.

24. A composition comprising a compound selected from the group consisting of:[3-(2-acetylamino-ethyl)-2-methyl-1H-indol-5-yl]-carbamic acid methyl ester; [3-(2-acetylamino-ethyl)-2-phenyl-1H-indol-5-yl]-carbamic acid methyl ester;[3-(3-acetylamino prop-1-yl)-1H-indol-5-yl]-carbamic acid methyl ester;N-[2-(5-methoxycarbonylamino-1H-indol-3-yl)-ethyl]-succinamic acid;[3-(2-acetylamino-ethyl)-1H-indol-5-yl]-carbamic acid allyl ester;[3-(2-acetylamino-ethyl)-1H-indol-5-yl]-carbamic acid 3-hydroxy-prop-1-yl ester; [3-(2-acetylamino-ethyl)-1H-indol-5-yl]-carbamic acid 2,3-dihydroxy-allyl ester; [3-(2-acetylamino-ethyl)-4-(1-methoxy-ethyl)-1-methyl-1H-indol-5-yl]-carbamic acid methyl ester N-[3-(2-acetylamino-ethyl)- 1H-indol-5-yl]-acetamide; [3-(2-acetylamino-ethyl)-1-benzyl-1H-indol-5-yl]-carbamic acid methyl ester; and (1-oxo-2,3,4,9-tetrahydro-1H-β-carbolin-6-yl)-carbamic acid methyl ester, and pharmaceutically acceptable vehicle or carrier.

* * * * *